United States Patent [19]

Bundy et al.

[11] Patent Number: 4,935,025
[45] Date of Patent: Jun. 19, 1990

[54] TRANSLUMINAL LYSING DEVICE

[76] Inventors: Mark A. Bundy, 101 Pine Dr., Covington, La. 70433; Larry J. Leyser, 700 E. E St., Rayne, La. 70578

[21] Appl. No.: 303,737
[22] Filed: Jan. 30, 1989
[51] Int. Cl.$^5$ .............................................. A61B 17/32
[52] U.S. Cl. ..................................... 606/180; 128/751; 128/753; 604/164
[58] Field of Search ...................... 128/751, 754, 755; 606/167, 168, 170, 180; 604/164, 264

[56] References Cited

U.S. PATENT DOCUMENTS

| | | | |
|---|---|---|---|
| 2,730,101 | 1/1956 | Hoffman | 128/300 |
| 3,683,891 | 8/1972 | Eskridge et al. | 128/751 |
| 3,732,858 | 5/1973 | Banko | 128/753 |
| 4,653,496 | 3/1987 | Bundy et al. | 128/305 |
| 4,745,919 | 5/1988 | Bundy et al. | 128/305 |

Primary Examiner—Mickey Yu
Assistant Examiner—Lynda M. Cofsky

[57] ABSTRACT

A surgical instrument consisting of an open flexible helix of wire attached to an exploratory catheter with a core or guidance wire (or other means) for contracting the device from an extracorporeal location for use in Transluminal Atherectomy and other similar situations for removing luminal protrusions or retrieving other useful samples.

4 Claims, 5 Drawing Sheets

1

TRANSLUMINAL LYSING DEVICE

FIELD OF INVENTION

The Transluminal Lysing Device relates mainly to the group of art in surgical instruments used for the removal of stenotic and occlusive lesions from the vascular lumens of living mammals (thrombectomy, atherectomy, endarterectomy).

BACKGROUND OF INVENTION

Due to the serious and debilitating nature of arteriosclerosis and its prevalence among the United States population many devices have recently been proposed and clinically tested that in some way relieve the detrimental effects of stenotic and occlusive lesions in the vascular system.

The "Transluminal Lysing Device" more specifically relates to surgical instruments capable of excising and removing from the body the biological material that makes up stenotic or occlusive lesions of biological lumens and are also operable from a location outside of the lumen or location outside of the body.

The following are prior art inventions having one or more similar characteristics or physical appearance attributes, or a similar resultant action to the invention described herein.

U.S. Pat. No. 4,030,503 Clark "Embolectomy Catheter" shows an open coil of round or half round wire and a central core wire used for support, but shows no method for enclosing material for removal from the body. Although its appearance is similar to the Transluminal Lysing Device, it does not perform the excision and removal process described by the invention herein.

U.S. Pat. No. 3,683,891 Eskridge et al., "Tissue Auger" shows an open coil of sharply disposed flat wire but shows no means for retaining tissue for removal other than friction along the smooth inner walls of the retainment chamber.

U.S. Pat. No. 4,653,496 Bundy et al., "Transluminal Lysing System" shows a flexible variably spaced coil of specially shaped and sharpened wire and a co-acting cutting cannula. Although some of the elements of the Transluminal Lysing Device are similar to those elements found in the "Transluminal Lysing System" the co-action of the elements work together in a very different manner to cause a different resultant action (i.e. the cutting mode) to achieve the same objectives of arterial patency and flow improvement.

Several U.S. Patents, (i.e. Banko, Kerfoot, Royce, et al.) show devices that remove tissue with an auger or auger and slot type arrangement. The baffle plate in the distal end of the Transluminal Lysing Device might be considered to operate in the fashion of an auger during engagement of the lesion material The auger type devices as a whole are inflexible and might not negotiate the tortuous blood vessels that need to be traversed to excise atherosclerotic and other lesions. The cutting action of most of these devices is that of a high speed rotary chipper or mill that creates small particles for removal through the auger. The creation of a large number of small particles in a blood vessel increases the chances for one of these particles to escape into the distal flow to cause embolic phenomenon, and is contrary to the objectives of this invention.

Technical and clinical information concerning a device called the Simpson Shaver was disseminated at the Texas Heart Institute Annual Interventional Cardiology Meeting in 1986 in Houston, Texas. The device has an inflexible tip that acts as a receiver for a rotating bolt or blade that has a sharp edge. Material is cut from the vessel wall and stored inside the end of the receiver. This tool is more selective than the Transluminal Lysing Device shown here. The selectivity is due to limitations of its construction in that it cannot remove material located directly in front of its distal end and is therefore incapable of removing total obstructions. Also due to the small portion of the tool's total volume that is used for material storage, several trips must be made to unload the storage compartment.

Although the above mentioned prior art shows one or more similar attributes in appearance or action to the Transluminal Lysing Device described herein. No prior art shows the unique cutting action or operational method, or material enclosure technique as shown in this invention.

The primary advantages of the present invention with respect to the prior art are brought about by its unique construction and method of operation The open coils of the Transluminal Lysing Device allow fast engagement with little torsional resistance since all cutting does not take place during rotation This also allows for deeper penetration. The lesion material which is still firmly attached to the lumen wall during engagement is more efficiently loaded relatively into the retainment chamber for subsequent excision and removal than in the prior art. Since the forces required for operating the tool are applied from outside the lumen, a large amount of energy can be expended and larger cutting forces applied during the excision process than is possible with similar prior art. The method described herein allows the excision process to be divided into discrete incremental parts engagement and excision. Energy for the former applied by torsional forces in the transport structure and energy for the latter applied by tensile and compressive forces in the core guide wire and support structure respectively. Another useful advantage is the high volumetric efficiency of this device. Through compression and containment during excision, the tool can clear a volume of material almost as large as its own closed volume. The device also clears a volume proportional to its length in one operation or trip (an operation involving the insertion and/or removal of a tool from a hole or shaft).

Other advantages of the invention will be apparent in the following specifications.

| FIELD OF SEARCH |||
|---|---|---|
| United States Classifications: 604/22, 46,47,49,52,53,164 |||
| 264,266,267,274,281; 128/305,305F,310,751,753,754,755. |||
| References: |||
| 2,850,007 | "Biopsy Device" | Lingley |
| 3,082,805 | "Tissue Macerator" | Royce |
| 3,683,891 | "Tissue Auger" | Eskridge |
| 3,732,858 | "Apparatus for removing blood clots . . . " | Banko |
| 3,749,085 | "Vascular Tissue Removing Device" | Willson |
| 3,945,375 | "Rotatable Surgical Instrument" | Banko |
| 3,976,077 | "Eye Surgery Device" | Kerfoot |
| 4,030,503 | "Embolectomy Catheter" | Clark |
| 4,177,797 | "Rotary Biopsy Device and Method . . . " | Baylis |
| 4,512,344 | "Arthroscopic Surgery Dissecting Apparatus" | Barber |

-continued

| FIELD OF SEARCH |
|---|
| United States Classifications: 604/22, 46,47,49,52,53,164 |
| 264,266,267,274,281; 128/305,305F,310,751,753,754,755. |

References:

| 4,653,496 | "Transluminal Lysing System" | Bundy |
|---|---|---|

OBJECTS OF THE INVENTION

The primary objective of this Invention is the removal of stenotic and occlusive lesions from vascular lumina by the least invasive and least traumatic means possible. Ideally this involves a peripheral percutaneous transluminal approach to the site of the lesion, its excision and subsequent improvement in blood flow parameters while the patient is conscious.

It is a further object of this invention to introduce a new and unique cutting method for use in the removal of stenotic and occlusive lesions.

It is a further object of this invention to entrap and enclose excised lesion material for removal from the lumen, drastically reducing the possibility of distal embolization of fragmented lesion material.

It is also an object of this invention to reduce morbidity and mortality in procedures for the removal or circumvention of stenotic and occlusive lesions and to reduce the need for traumatic alternative procedures such as a vascular bypass grafting surgery.

It is a further object of this invention to reduce the cost of treatment of vascular diseases that cause the formation of stenotic and occlusive lesions in the vascular system.

Further objects and advantages of the new and unique concept described herein will be more apparent after a study of the following drawings, descriptions, and operational examples.

DETAILED DESCRIPTION OF DRAWINGS FIG.

1 is an enlarged 30 degree isometric projection of the

Figure 2:
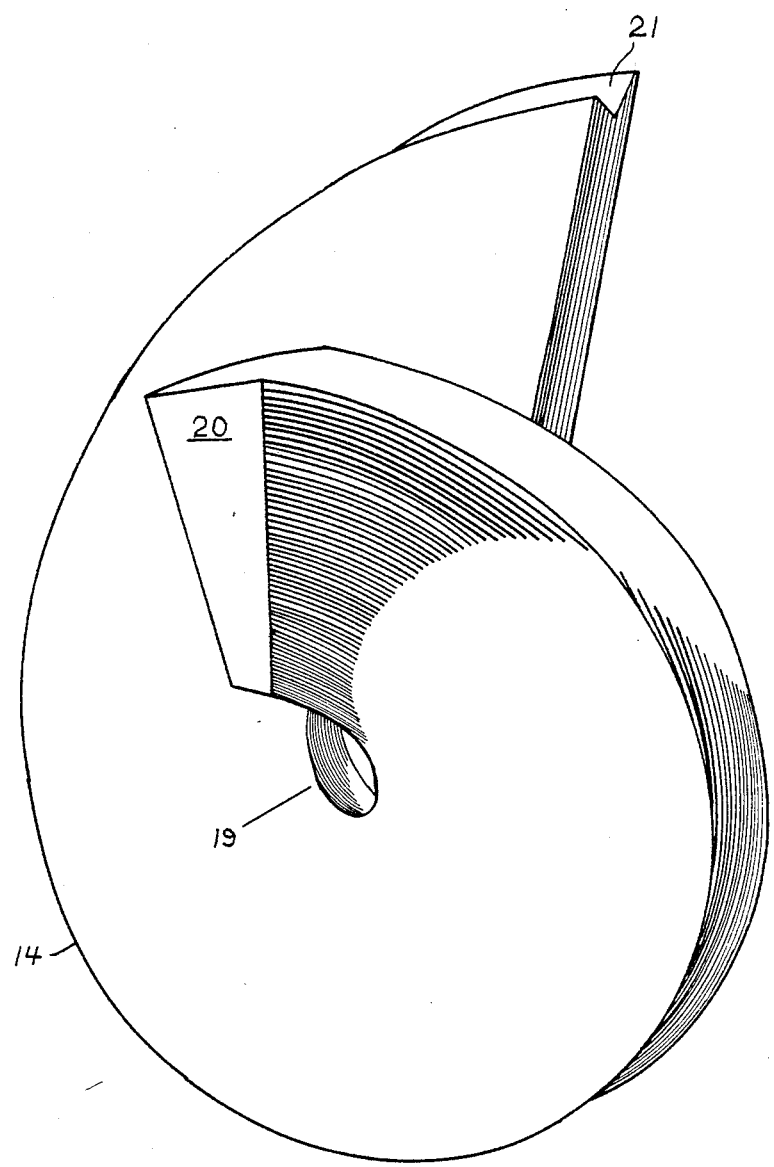
Figure 3:
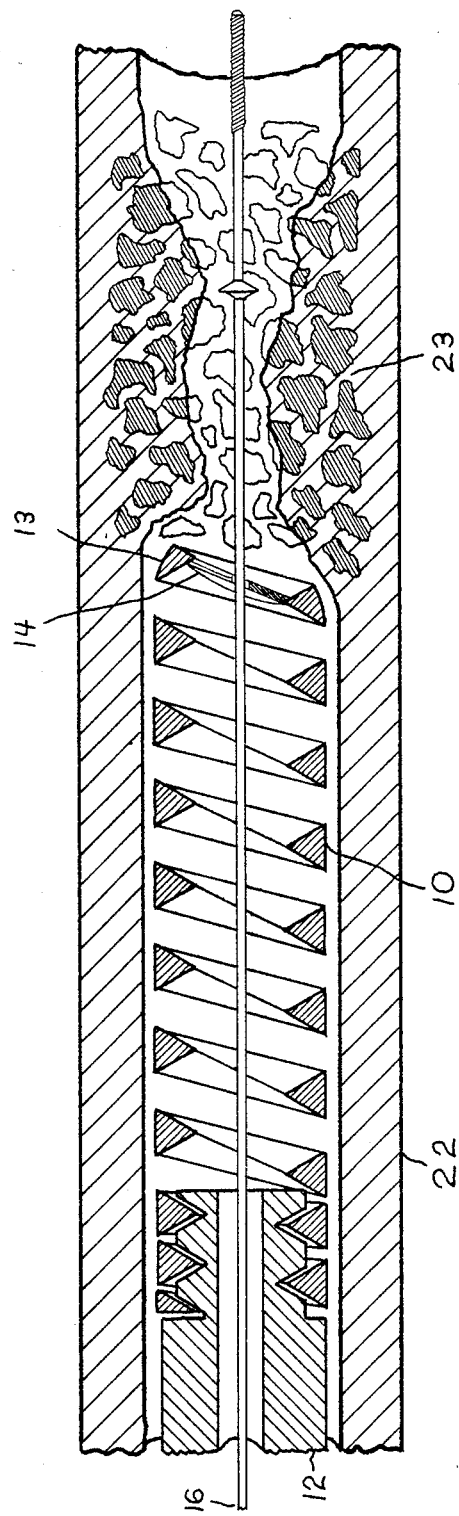
Figure 4:
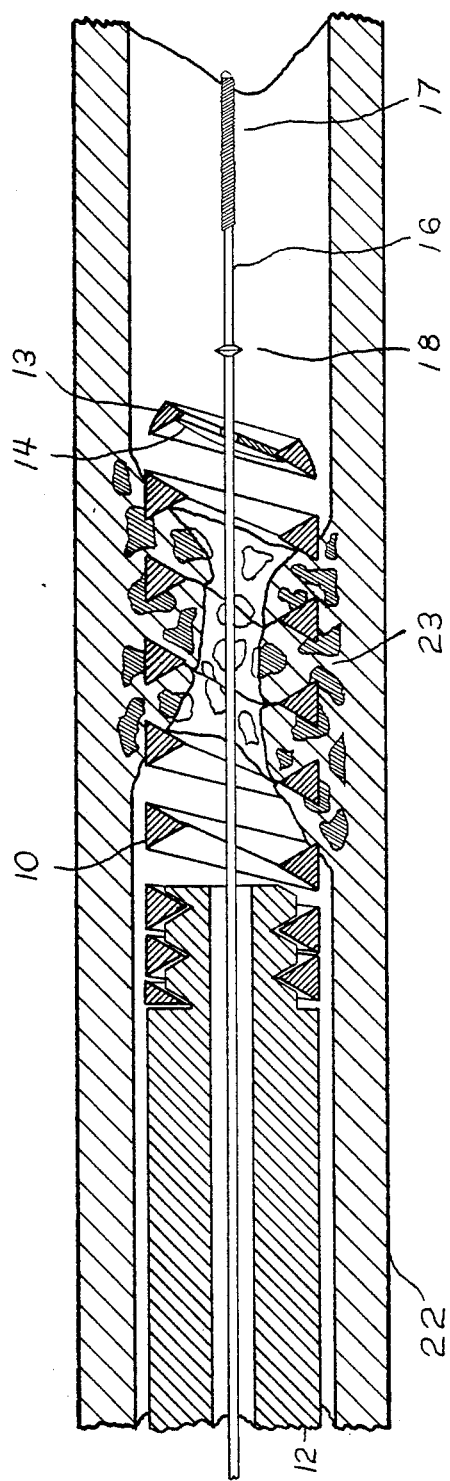
Figure 5:
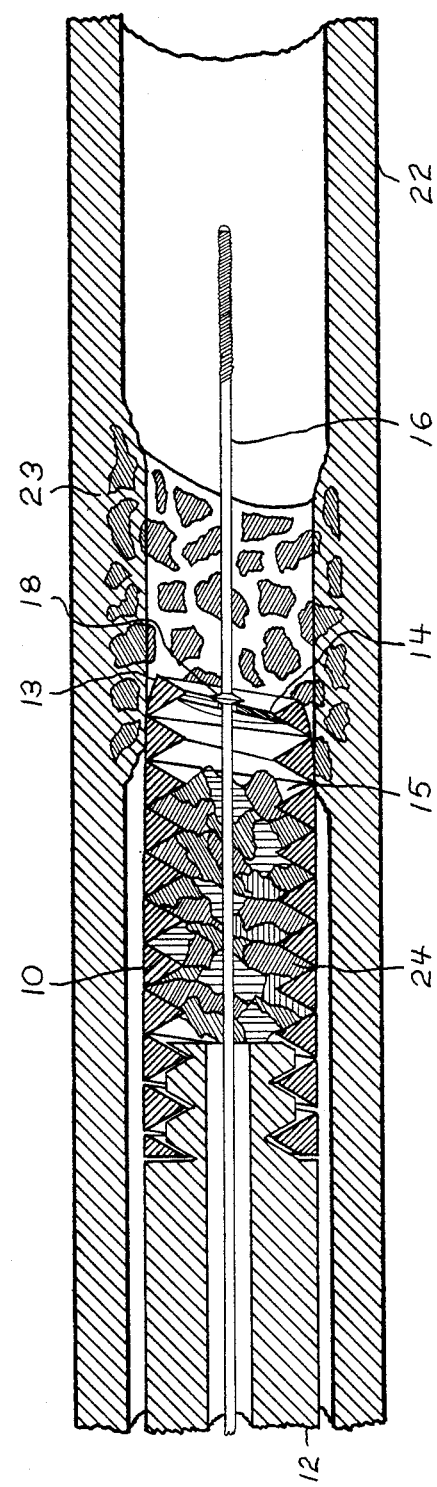

Transluminal Lysing Device with an operational core and guidance wire; FIG. 2 is an enlarged 30 degree oblique projection of the baffle plate, shown prior to installation and welding; FIG. 3 is an enlarged cross section view of the Transluminal Lysing Device revealing the core guidance wire, shown just prior to engagement of a vascular lesion. FIG. 4 is an enlarged cross section view of the Transluminal Lysing Device revealing the core guidance wire, shown just after rotational engagement of a vascular lesion. FIG. 5 is an enlarged cross section view of the Transluminal Lysing Device revealing the core guidance wire, shown after excision and during removal of excised lesion material from a vascular lumen;

DETAILED PHYSICAL DESCRIPTION OF THE DRAWINGS

Figure 1:
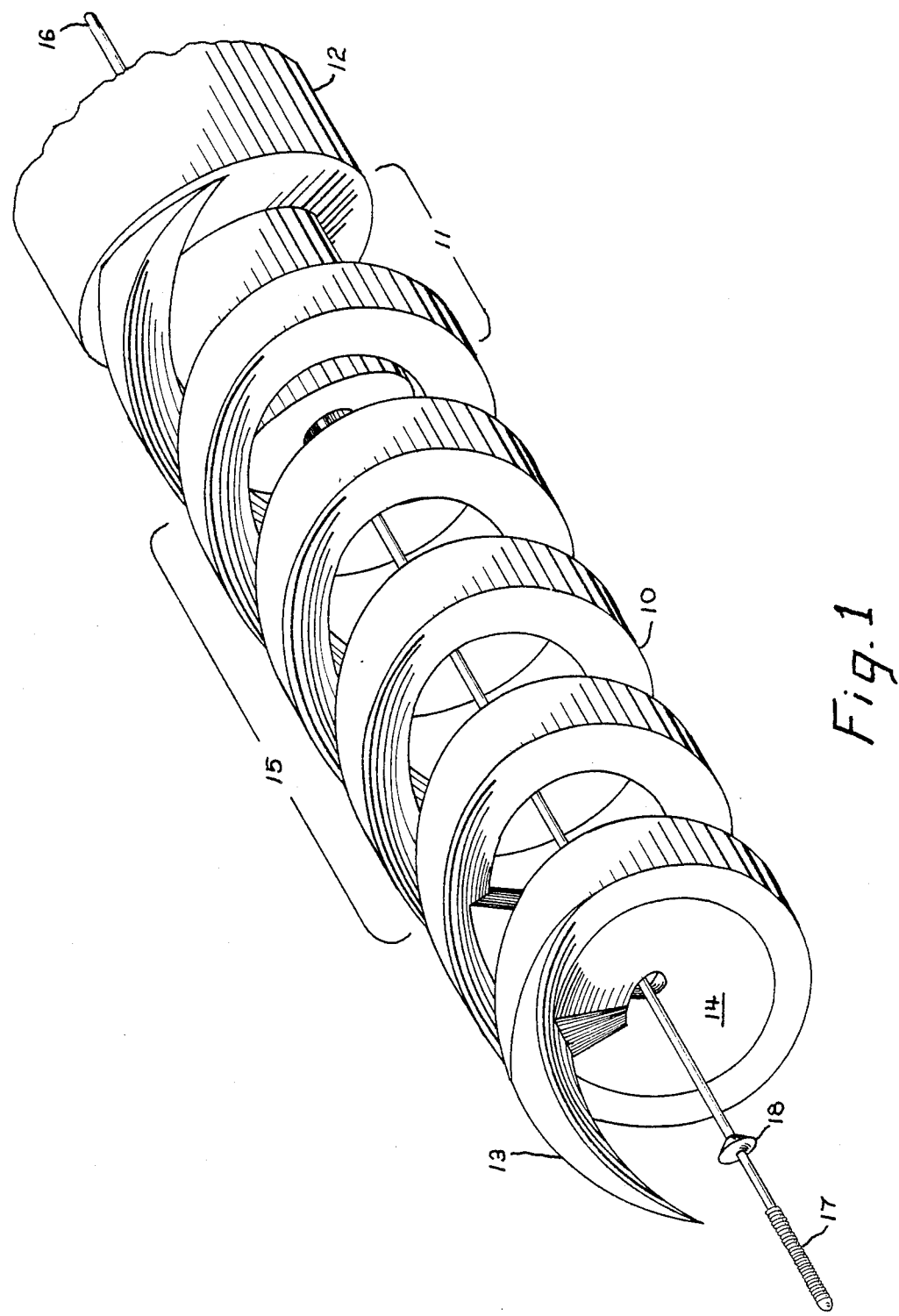

Referring to FIG. 1 of the drawings The Transluminal Lysing Device cutting helix 10 is formed by coiling specially shaped and sharpened wire around a mandrel in the manner of a spring as shown in the prior art, however the adjacent coils of the Transluminal Lysing Device are placed spacedly at an axial pitch distance that approximates 2 or more times the width of the wire over the working length 15 of the tool.

The non working length 11 being that part where the coil is bonded or other wise connects with its support and transport structure 12 where axial pitch has no particular importance.

The cylindrically shaped coil thus formed is the cutting helix 10 which has a proximal and distal end. The proximal end is so disposed as to be bonded on a support and transport means 12. The support and transport means 12 is a generally cylindrical support but can be of any otherwise useful configuration. The last distal coil or entrance tip 13 is sharpened at its distal extremity so as to initially pierce and engage lesion material upon rotation into a lesion or other material. Further rotation causes lesion material to move relatively between the edges of adjacent coils and between the vertical walls formed by the baffle plate 14.

The baffle plate 14 acts as a trap door and is located at the distal end of the cutting helix providing an entry way for material into the central space within the cutting helix 10, when the tool is rotated into lesion material. When the working length 15 is contracted by use of the core-guidance wire 16 or other means, the baffle plate 14 deforms into a disk shaped obstruction blocking off the entry way for material at the distal end of the cutting helix 10 and entrapping lesion material inside the Transluminal Lysing Device. During this contraction, the sharp edges at the outer diameter of the cutting helix coils along the working length 15 impinge upon the engaged tissue and sever this tissue from the lumen wall, as the sharp edges of adjacent coils come into contact with each other. FIG. 2 shows in more detail the preferred embodiment of the baffle plate 14 showing a wire clearance passageway 19, a sharpened leading edge 20, and an attachment groove 21. The baffle plate 14 is attached to the distal end or entrance tip 13 of the cutting helix 10 by electron beam welding, lasing, brazing, chemical bonding, or other known means. During lesion engagement, the baffle plate 14 acts in a manner analogous to an earth boring auger or a single flight of a material transport auger.

Contraction of the working length 15 of the tool body to operate the cutting and entrapping mechanism can be accomplished by means other than a core guide wire. Temperature sensitive phase change or shape memory alloys could be employed to form the cutting helix, and various means such as lasing, electric resistance, or fluid circulation to alter the alloy's temperature to cause contraction or expansion could be facilitated. These emerging technologies are expensive and since one of the primary objectives of the invention is the reduction of treatment costs the preferred embodiment will show a core guidance wire used as a means for effecting contraction and closure of the Transluminal Lysing Device.

The trap door function of the baffle plate 14 could be carried out by various other means having other advantages such as multiple flights for better sealing, special edge configurations to aid in the process of bonding the plate to the coil or special guides to keep the core wire from becoming entangled or otherwise interfering with the devices operation.

The core guidance wire 16 shown in FIG. 1 used to contract the cutting helix length has what is known in the art as a floppy radiopaque tip 17 to aid in guidance but has an added ability to engage itself by means of wire stop 18 with the baffle plate 14 and is of sufficient tensile strength to apply contact forces to the baffle plate necessary to effect closure of the cutting helix body 10 along the working length 15 and deformation of the baffle plate 14.

To ease operation of the device some sort of take up device or racheting mechanism can be applied to the core wire with respect to the cutting helix support structure so as to hold the cutting helix in its contracted mode and prevent the accidental opening of the device once it has been loaded.

OPERATIONAL DESCRIPTION

Methods for pre-treatment, access, and visualization as used in intraluminal procedures of this nature are known in the art, but to clarify, we reiterate that the procedure is carried out by operators acting from a location outside of the afflicted lumen or outside of the body containing the affected lumen.

After pre-treatment, access and visual localization, the core-guidance wire 16 is inserted into the lumen 22 shown in FIG. 3 and is then translated flexibly to the site of the lesion 23 and across it. The cutting helix 10 is then inserted into the lumen and translated using an over the wire technique to the site of lesion and in such a manner that the entrance tip 13 abuts the lesion material. Other useful delivery systems such as sheaths or external guiding catheters such as known in the art could be used to facilitate locating the device at the desired location.

Referring to FIG. 4, the cutting helix 10 is then rotated to engage and lyse its way through the lesion 23. Due to the helical nature of the cutting helix 10, rotation causes the tool to translate itself across the lesion relative to the position of the lesion, or you may say it is self advancing during rotational engagement.

Due to the uniform spacing between adjacent coils of the cutting helix 10, no material is completely dislodged from the vessel wall during engagement or rotationally induced translation. The material that is still attached and supported by the lumen wall is well suited to pass between the opening in the baffle plate 14 and progress toward the rear or proximal portion of the cutting helix 10. When the distal end of the lesion 23 is reached by the distal entrance tip 13, engagement is complete. It is noted here that although the length of the tool is not a parameter of primary importance, the length of the tool should be sufficient to totally engage over its working length the lesion chosen for removal and not so long as to cause tearing actions as might be encountered during contraction of an overly long cutting helix 10.

Referring now to FIG. 5, the core wire 16 is then retracted sliding through the center of the cutting helix 10 until the wire stop 18 contacts the baffle plate 14. Further retraction of the core wire 16 then causes the contraction of the cutting helix 10 and deformation of the baffle plate 14 so as to complete the excision of the remaining lesion material from the lumen wall by the cutting helix 10 entrapping the excised material in an area within the cutting helix and behind the baffle plate 14 and thereby binding the volume of excised material within the cutting helix 10 along the contracted working length 15. At this time, lesion material 24 has been excised and stored within the tool and is ready for removal from the lumen 22. It is important to note the simplicity and ease of operation during removal of the lesion. This is important because of the fact that during engagement of the lesion and prior to its removal; the lumen is obstructed by the lesion, the device, the core wire, and transport catheter. These obstructions restrict the flow of blood along the distal path of the lumen. The shorter the time interval that blood flow is restricted, the less likely ischemic complications to the patient will occur. Visualization of the lumen after lesion removal will then demonstrate whether patency or dynamic flow improvements have been effected.

In Transluminal Lysing Devices of larger diameter the core-guidance wire could take the form of a tube that would allow the in process measurement of distal hemodynamic pressure in such a manner that the system's effects on flow parameters could be monitored.

While the embodiment of the device herein described is especially suited for operation in the vascular system, the inventive concepts and constructions disclosed are capable of many other uses in biological lumens or industrial lumens and should not be construed as a limiting set of circumstances.

We claim:

1. A Transluminal Lysing Device for the removal of stenotic and occlusive lesions from vascular lumens or for the useful sampling of any other material comprising:

a cylindrical cutting helix formed by coiling a strip of material in a helical fashion so as to form an open coil, each adjacent winding being separated spacedly from the next winding so as to allow the unobstructed penetration of lesion material when the cutting helix is rotated into such material, a proximal and distal end of said cutting helix, a sharpened entrance tip at said distal end of said cutting helix formed by sharpening the most distal portion of the last distal winding of the cutting helix to aid the cutting helix in initially piercing material and guide its subsequent engagement, a means for support, rotation, translation of and communication with said cutting helix, being of sufficient length to allow operation of the cutting helix from a remote location outside of the lumen, a means for contracting the length of the cutting helix so as to close the spaces between adjacent windings of said cutting helix and thereby causing excision and subsequent enclosure of excised lesion material within the center of said cutting helix, contracting means being operable from a location outside of the affected lumen.

2. A Transluminal Lysing Device as in claim 1 further comprising:

a trap door means located at the distal end of the cutting helix to allow lesion material to enter the cutting helix upon initial rotations and to later obstruct the release of enclosed lesion material from within the center of said cutting helix when the cutting helix is contracted.

3. A Transluminal Lysing Device as in claim 2 wherein the means for contracting the cutting helix's length further comprises:

a flexible shaft positioned concentrically inside the cutting helix and capable of relative internal motion in the proximal and distal directions having means to co-act with the cutting helix or trap door means so as to effect the contraction of the length of the cutting helix, 4. A Transluminal Lysing Device as in claim 3 wherein the trap door means further comprises:

a trap door means further comprising;

an annular disk of flexible material having been cut transversely along a radial line from the inner diameter to the outer diameter, outer circumference of said disk being disposed for attachment to the last distal coil of a cutting helix, along a helical connection pathway so that an opening is formed where the radial cut is made, the size of said opening or space between the cut ends of the annular disc being equal to the pitch of the coil less the disc thickness.

* * * * *